(12) United States Patent
Gaylord et al.

(10) Patent No.: US 6,379,321 B2
(45) Date of Patent: *Apr. 30, 2002

(54) PLANTAR FASCITIS SUPPORT APPARATUS

(75) Inventors: Robert Scott Gaylord, Matthews; Donald Earl Griffin, Rural Hall, both of NC (US)

(73) Assignee: Medical Specialties, Inc., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/783,632

(22) Filed: Feb. 14, 2001

Related U.S. Application Data

(63) Continuation of application No. 09/365,670, filed on Aug. 2, 1999, now Pat. No. 6,228,045.

(51) Int. Cl.[7] .................................................. A61F 5/00
(52) U.S. Cl. .............................. 602/27; 602/26; 602/29
(58) Field of Search ............................ 602/26, 27, 29, 602/60, 61, 63, 65

(56) References Cited

U.S. PATENT DOCUMENTS

| | | | | |
|---|---|---|---|---|
| 3,506,000 A | * | 4/1970 | Baker | 128/166 |
| 3,699,959 A | * | 10/1972 | Garrahan et al. | 602/65 |
| 4,393,522 A | * | 7/1983 | Calabrese | 2/336 |
| 4,597,395 A | * | 7/1986 | Barlow et al. | 602/27 |
| 4,966,134 A | * | 10/1990 | Brewer | 602/27 |
| 5,090,404 A | * | 2/1992 | Kallassy | 602/65 |
| 5,957,874 A | * | 9/1999 | Klein | 602/23 |
| 6,228,045 B1 | * | 5/2001 | Gaylord et al. | 602/27 |

* cited by examiner

Primary Examiner—Michael A. Brown
Assistant Examiner—Lalita M Hamilton
(74) Attorney, Agent, or Firm—Adams, Schwartz & Evans, P.A.

(57) ABSTRACT

A plantar fascitis foot support apparatus, including a support strap for being positioned in a generally U-shaped configuration along the medial and lateral aspects of the ankle and extending under and supporting the plantar fascia region of the foot. An ankle-encircling retention strap is attached by its opposite ends to the support strap at a substantially right angle thereto for retaining the support strap in a supporting position against the plantar fascia region. The support strap includes an inelastic segment and at least one attached elastic segment for providing controlled stretch of the support strap during placement on the foot and during subsequent movement of the foot while the support is in place. Complementary and releasably-adjustable fastener elements are carried by the retention strap and the support strap for permitting lengthwise adjustment of the support strap relative to the plantar fascia region of the foot. The fastener elements include a first fastener element carried by an outer surface of the retention strap, a second fastener element carried by an inner surface of the support strap for being adjustably-mated with the first fastener element for retaining the support strap and the retention strap in a desired position relative to each other, and a third fastener element carried on an outer surface of the support strap. A fastener cover is carried by the retention strap and has a fourth fastener element carried on an inner surface thereof for mating with the third fastener element of the support strap.

12 Claims, 6 Drawing Sheets

PLANTAR FASCITIS SUPPORT APPARATUS

This application is a continuation of U.S. Ser. No. 09/365,670 filed on Aug. 2, 1999, now U.S. Pat. No. 6,228,045.

TECHNICAL FIELD AND BACKGROUND OF THE INVENTION

This invention relates to a plantar fascitis support apparatus with support and adjustment features which enhance the comfort, adjustability and support provided by the apparatus. Plantar fascitis is a medical condition characterized by a tear in the arch ligament, or plantar fascia, on the bottom of the human foot. The plantar fascia extends from the base of the heel bone to each of the toes of the foot. Plantar fascitis results when, either suddenly or gradually, motion and/or lack of arch support causes the flattening of the arch or the spreading of the toes such that sufficient pressure is exerted on the bottom of the foot to tear the plantar fascia. Injury often occurs as the result of hyperextension of the toes in the upward direction during exercise.

Plantar fascitis can be quite debilitating in that everyday activities such as walking and standing are very painful. Typically, most pain is experienced in the heel area, where the plantar fascia attaches to the heel and where tears and separations often occur. Plantar fascitis is most easily treated—and, from the patient's perspective, most efficiently treated—by wearing a foot support especially designed to help heal the condition while permitting the patient to remain relatively mobile. Some plantar fascitis supports are designed for use only when the patient is resting, i.e., when little or no weight is being applied to the injured foot. Other plantar fascitis supports, such as the present invention, can be worn by the patient during activity as well as when at rest.

Some conventional supports are either too bulky to be easily worn with footwear, or so flimsy that too little support is provided, inadequate adjustment is provided, or the support loses proper adjustment during wear. The present invention provides a plantar fascitis support apparatus which addresses these problems.

SUMMARY OF THE INVENTION

Therefore, it is an object of the invention to provide a plantar fascitis support apparatus which is lightweight and comfortable within conventional footwear.

It is another object of the invention to provide a plantar fascitis support apparatus which has a wide range of adjustment.

It is another object of the invention to provide a plantar fascitis support apparatus which remains in adjustment during extended wear.

It is another object of the invention to provide a plantar fascitis support apparatus wherein the hook elements of conventional hook-and-loop fastener elements are covered and therefore do not contact the skin or clothing.

These and other objects of the present invention are achieved in the preferred embodiments disclosed below by providing a plantar fascitis foot support apparatus, including a support strap for being positioned in a generally U-shaped configuration along the medial and lateral aspects of the ankle and extending under and supporting the plantar fascia region of the foot. An ankle-encircling retention strap is attached by its opposite ends to the support strap at a substantially right angle thereto for retaining the support strap in a supporting position against the plantar fascia region. The improvement comprises the support strap including an inelastic segment and at least one attached elastic segment for providing controlled stretch of the support strap during placement on the foot and during subsequent movement of the foot while the support is in place. Complementary and releasably-adjustable fastener elements are carried by the retention strap and the support strap for permitting lengthwise adjustment of the support strap relative to the plantar fascia region of the foot. The fastener elements include a first fastener element carried by an outer surface of the retention strap, a second fastener element carried by an inner surface of the support strap for being adjustably-mated with the first fastener element for retaining the support strap and the retention strap in a desired position relative to each other, and a third fastener element carried on an outer surface of the support strap. A fastener cover is carried by the retention strap and has a fourth fastener element carried on an inner surface thereof for mating with the third fastener element of the support strap.

According to one preferred embodiment of the invention, the first and second fastener elements comprise complementary hook and loop fastener elements.

According to another preferred embodiment of the invention, the third and fourth fastener elements comprise complementary hook and loop fastener elements for increasing the shear force required for separation of the support strap and the retention strap for covering any of the third fastener elements exposed on the outer surface of the retention strap against contact with the skin of the wearer.

According to yet another preferred embodiment of the invention, a pad is provided for being positioned on the support strap for engaging the plantar fascia region of the foot when the foot support is in place on the foot.

According to yet another preferred embodiment of the invention, adjustment elements are provided for releasably adjusting the pad on the strap.

Preferably, the adjustment elements comprise complementary hook and loop fastener elements carried respectively by the pad and the support strap.

According to one preferred embodiment of the invention, a support strap is provided for being positioned in a generally U-shaped configuration along the medial and lateral aspects of the ankle and extending under and supporting the plantar fascia region of the foot. An ankle-encircling retention strap is attached by its opposite ends to the support strap at a substantially right angle thereto for retaining the support strap in a supporting position against the plantar fascia region. The improvement comprises the support strap including an inelastic segment and at least one attached elastic segment for providing controlled stretch of the support strap during placement on the foot and during subsequent movement of the foot while the support is in place.

According to another preferred embodiment of the invention, a support strap is provided for being positioned in a generally U-shaped configuration along the medial and lateral aspects of the ankle and extending under and supporting the plantar fascia region of the foot. An ankle-encircling retention strap is attached by its opposite ends to the support strap at a substantially right angle thereto for retaining the support strap in a supporting position against the plantar fascia region. The improvement comprises complementary and releasably-adjustable fastener elements carried by the retention strap and the support strap for permitting lengthwise adjustment of the support strap relative to the plantar fascia region of the foot. The fastener elements include a first fastener element carried by an outer surface of the retention strap, a second fastener element carried by an inner surface of the support strap for being adjustably-mated with the first fastener element for retaining the support strap and the retention strap in a desired position relative to each other, a third fastener element carried on an outer surface of the support strap, and a fastener cover carried by the retention strap and having a fourth fastener element carried on an inner surface thereof for mating with the third fastener element of the support strap.

According to yet another preferred embodiment of the invention, a support strap is provided for being positioned in a generally U-shaped configuration along the medial and lateral aspects of the ankle and extending under and supporting the plantar fascia region of the foot. An ankle-encircling retention strap is attached by its opposite ends to the support strap at a substantially right angle thereto for retaining the support strap in a supporting position against the plantar fascia region. The improvement comprises first complementary and releasably-adjustable fastener elements carried by an outer surface of the retention strap and an inner surface of the support strap for permitting lengthwise adjustment of the support strap relative to the plantar fascia region of the foot, and second complementary and releasably-adjustable fastener elements carried by an outer surface of the support strap and an inner surface of a cover carried by the retention strap for providing enhanced attachment force between the retention strap and the support strap.

Preferably, the cover is attached to the retention strap at one end of the cover.

Preferably, the first and second fastener elements comprise complementary hook and loop elements.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
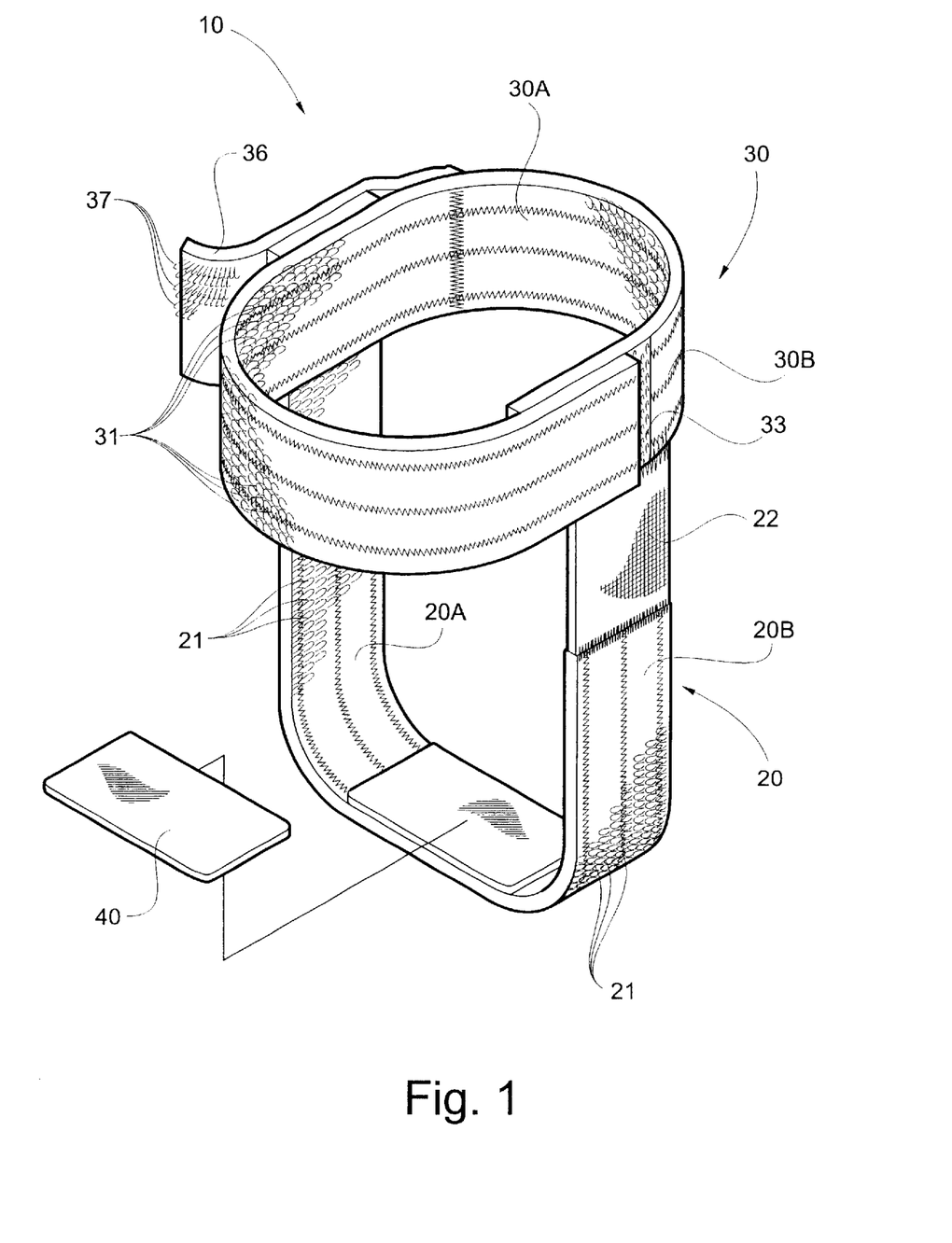
FIG. 1 is a perspective view of a plantar fasciitis support apparatus according to an embodiment of the invention as positioned on a foot, with the foot omitted for clarity.

Referring now specifically to the drawings, a plantar fasciitis support apparatus according to the present invention is illustrated in FIG. 1 and shown generally at reference numeral 10. The plantar fasciitis support apparatus 10 is constructed of two principal elements, a support strap 20 and a retention strap 30 which intersect and connect with each other at a substantially right angle to each other. As is shown in FIGS. 2–5, the support strap 30 extends in a generally "U" shaped configuration under the bottom of the foot and extends upwardly along the medial and lateral aspects of the foot. Optionally, a pad 40 is positioned in the bottom of the "U" and directly engages the plantar fascia in the arch of the foot anterior of the heel. The support strap 30 is maintained in its proper support position by the retention strap 20, which encircles the ankle. Proper adjustment is essential if the plantar fasciitis support apparatus 10 is to perform its intended therapeutic functions.

Both the support strap 20 and retention strap 30 are preferably constructed of narrow, inelastic straps of synthetic material such as nylon, polyester or polypropylene, with a mass of closely-spaced, relatively long loops 21 and 31, respectively, preferably covering respective inner and outer surfaces 20A, 20B, 30A, 30B. Such straps are typically woven or knitted with terry loops on the faces of the fabric, and are designed specifically to serve as the female, loop part of conventional hook-and-loop fastening elements.

Support strap 20 includes an elastic segment 22, one end of which is attached by, for example, sewing stitches, to retention strap 30. The other end of the elastic segment 22 is attached by sewing stitches to one end of the support strap 20. This permanent attachment maintains the entire plantar fasciitis support apparatus 10 as a unit when not in use and prevents complete separation or loss of one or the other straps when not in use. The elastic segment 22 permits a desired degree of tension to be placed on the support strap 20 when it is attached to the retention strap 30, as described below.

Figure 2:
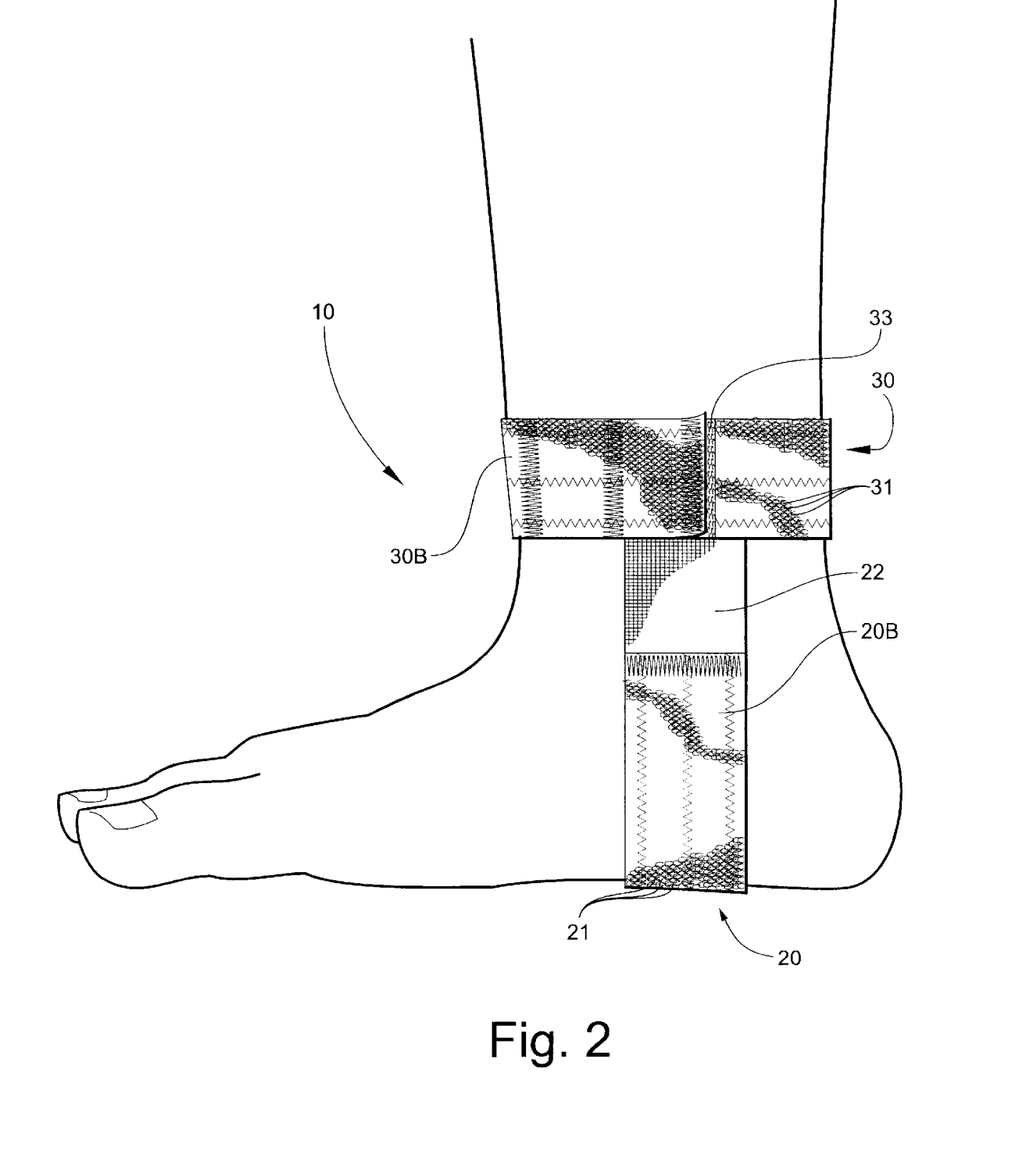
FIG. 2 is a side elevation of the medial aspect of the foot, ankle and lower leg with the plantar fasciitis support apparatus shown in FIG. 1 in place on the foot.
Figure 3:
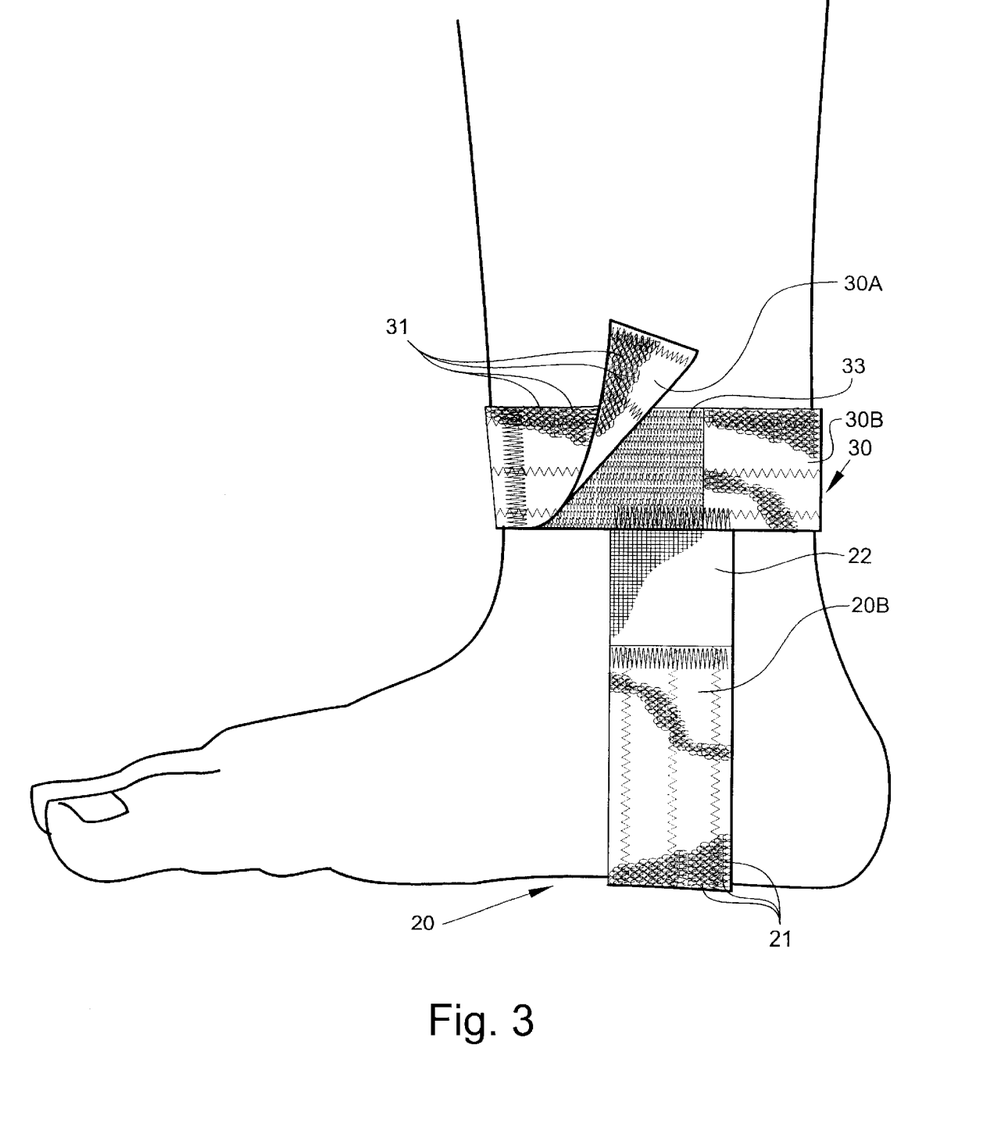
FIG. 3 is a view similar to FIG. 2, with an end of the retention strap peeled away for clarity.
Figure 4:
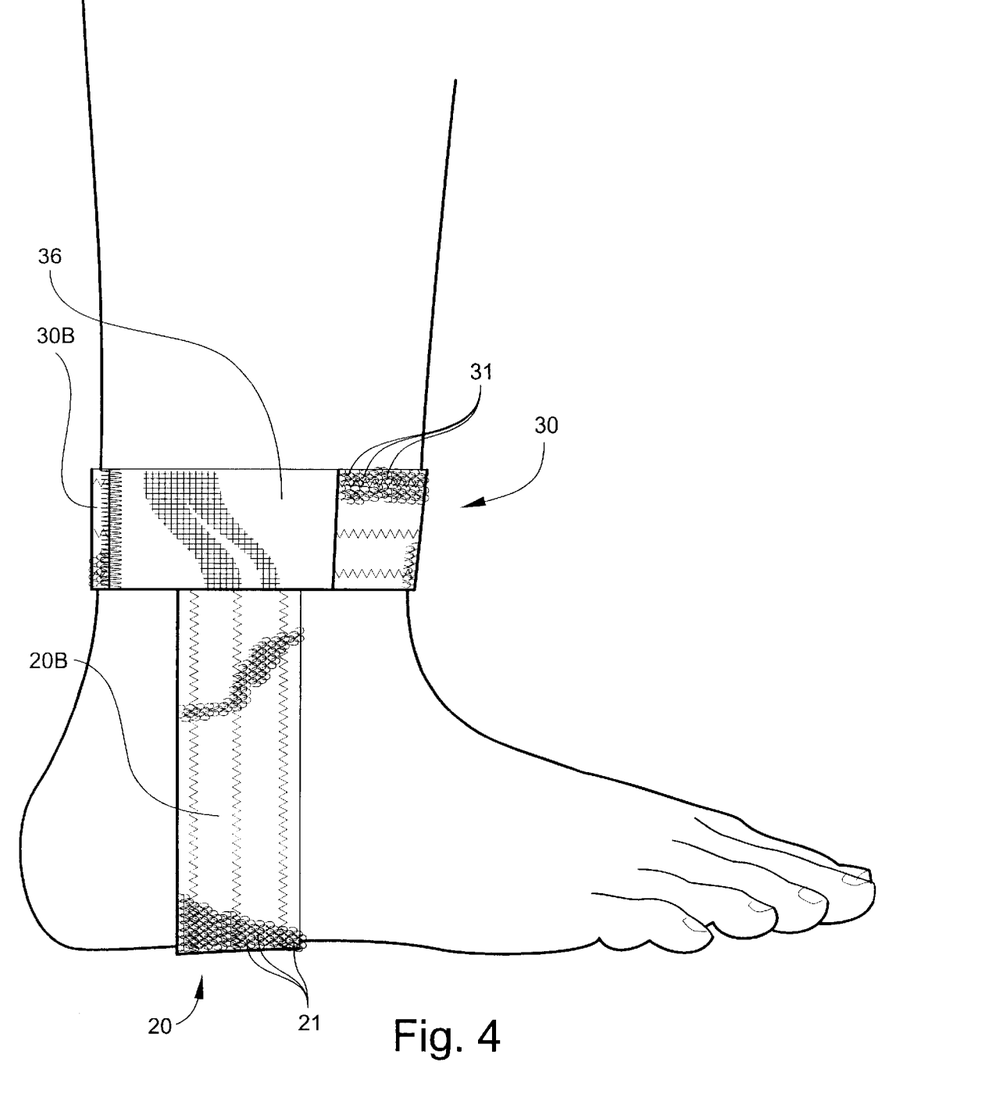
FIG. 4 is a side elevation of the lateral aspect of the foot, ankle and lower leg with the plantar fasciitis support apparatus shown in FIG. 1 in place on the foot.

Loops 21 and 31 form one part of two-part attachment elements, the other half of which are formed of complementary plastic hooks. As is best shown in FIGS. 2 and 3, retention strap 30 includes a patch 33 of hook elements positioned on the outer surface 30B of the retention strap 30 adjacent one end. Proper position of the retention strap 30 is maintained by lapping the other end of the retention strap 30 over the patch 33 of hook elements and pressing the two elements together.

Figure 5:
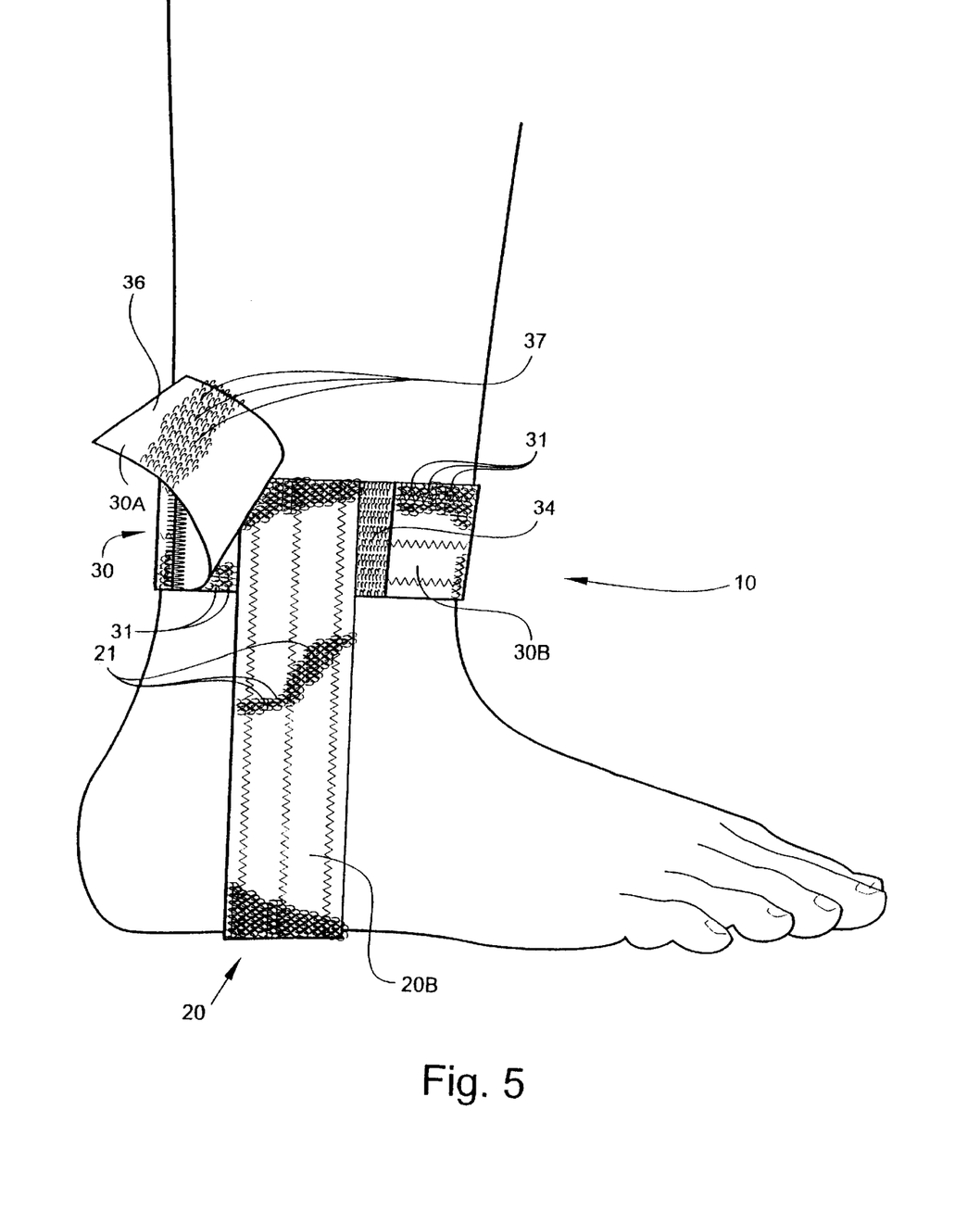
FIG. 5 is a view similar to FIG. 4, with the cover attached to the retention strap peeled away for clarity.

As is best shown in FIG. 5, the support strap 20 is attached to the retention strap 30 by means of a patch 34 of hooks positioned on the outer surface 30B of the retention strap 30 intermediate its opposing ends. After the support strap 20 is passed under the foot, the support strap 20 is length-adjusted to exert the proper pressure on the plantar fascia. Adjustment is facilitated by the elastic segment 22. See FIG. 2. While holding the support strap 20 in the desired position, the free end area of the inner surface 20A of the support strap 20 which, as noted above, is covered with loops 21, is pressed against the patch 34 of hooks on retention strap 30 to fasten the retention strap 30 and the support strap 20 together.

The elastic segment 22 exerts a pull on the support strap 20 which comprises a shearing force against the hooks 34 and the entangled loops 31 at the point of connection between the support strap 20 and the retention strap 30. This shearing force is resisted more effectively by securing both surfaces of the support strap 20 to the retention strap 30. This is accomplished by providing a cover 36 which is attached by, for example, sewing stitches, to the retention strap 30 adjacent one end of the patch 34 of hooks. The interior side of the cover 36 comprises hooks 37 which entangle with and attach to the loops 21 on the outer surface 20B of the support strap 20. After the inner surface 20A of the support strap 20 is attached to the retention strap 30, as described above, the cover 29 is extended over the outer surface 20B of the support strap 20, thus attaching both inner and outer surfaces 20A and 20B of the support strap 20 to the retention strap 30.

Thus, significant additional resistance to shear forces exerted on the retention strap 30 by the support strap 20 is provided without the need to widen the straps or otherwise add significantly to the weight or bulk of the plantar fascitis support apparatus.

Additionally, the cover 36 can easily be made long enough to cover any of the exposed hooks on patch 34, thus preventing contact between exposed hooks of the patch 34 and skin or clothing. The cover 36 preferably has a smooth, snag-resistant outer surface so that any contact with skin or clothing does not result in discomfort.

Figure 6:
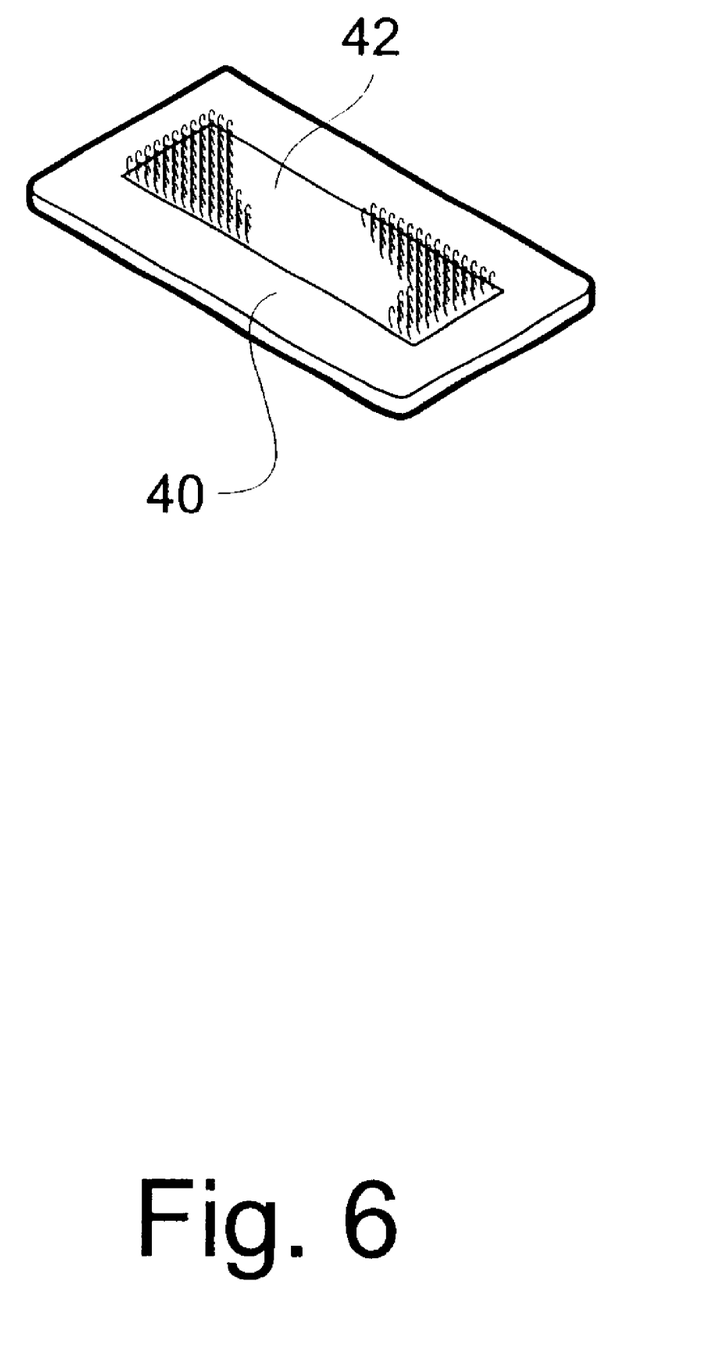
FIG. 6 is a view of the bottom surface of the pad which is attached to the support strap and which supports the plantar fascia when the plantar fasciitis support apparatus is in proper position on the foot.

The pad 40 is preferably adjustable and removable. For this purpose, a patch 42 of hooks is attached by adhesive or other means to one surface of the pad 40, as shown in FIG. 6. The patch 42 cooperates with the loops 21 on the inner surface 20A at the bottom of the "U" to secure the pad 40 is the desired position. The pad 40 is fabricated of a suitable weight and density of a foam material. The pad 40 can be easily repositioned when desired or removed altogether for replacement or when laundering the plantar fascitis support apparatus.

A preferred embodiment of the plantar fascitis support apparatus is set out below:

| | |
|---|---|
| Length of support strap 20 | 13¾ inches |
| Length of elastic segment 22 | 1¾ inches |
| (flaccid) | 1¾ inches |
| (max elongation) | 3 inches |
| Length of inelastic segment of support strap 20 | 12 inches |
| Thickness of support strap 20 and retention strap 30 | ⅛ inch (approx) |
| Length of retention strap 30 | 15 inches |
| Length of cover 36 | 4½ inches |
| Pad 40 dimensions | 1¼ × 3½ × ⅛ inches |

Of course, many other variations are possible, including different constructions for men, women and children. While hook-and-loop fasteners are considered to be most desirable and preferred, other types of "touch" fasteners are also suitable, including "mushroom" and "Christmas tree" types of touch fasteners. In addition, snaps, buttons, strap and buckle elements and other types of fasteners are suitable.

A plantar fascitis support apparatus is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

We claim:

1. A plantar fascitis foot support apparatus, comprising:
   (a) a support strap for being positioned in a generally U-shaped configuration along the medial and lateral aspects of the ankle and extending under and supporting the plantar fascia region of the foot;
   (b) an ankle-encircling retention strap attached by its opposite ends to the support strap at a substantially right angle thereto for retaining the support strap in a supporting position against the plantar fascia region;
   (c) said support strap including an inelastic segment and at least one attached elastic segment for providing controlled stretch of the support strap during placement on the foot and during subsequent movement of the foot while the support is in place; and
   (d) complementary and releasably-adjustable fastener elements carried by said retention strap and said support strap for permitting lengthwise adjustment of the support strap relative to the plantar fascia region of the foot for retaining the support strap and the retention strap in a desired position relative to each other.

2. A plantar fascitis foot support apparatus according to claim 1, wherein said fastener elements comprise complementary hook and loop fasteners.

3. A plantar fascitis foot support apparatus according to claim 1, wherein said fastener elements comprise complementary hook and loop fastener elements for increasing the shear force required for separation of the support strap and the retention strap.

4. A plantar fascitis foot support apparatus according to claim 1, and including a pad positioned on the support strap for engaging the plantar fascia region of the foot when the foot support is in place on the foot.

5. A plantar fascitis foot support apparatus according to claim 4, and including adjustment elements for releasably adjusting the pad on the strap.

6. A plantar fascitis foot support apparatus according to claim 4, wherein said adjustment elements comprise complementary hook and loop fastener elements carried respectively by said pad and said support strap.

7. A plantar fascitis foot support apparatus, comprising:
   (a) a support strap for being positioned in a generally U-shaped configuration along the medial and lateral aspects of the ankle and extending under and supporting the plantar fascia region of the foot;
   (b) an ankle-encircling retention strap attached by its opposite ends to the support strap at a substantially right angle thereto for retaining the support strap in a supporting position against the plantar fascia region; and
   (c) said support strap including an inelastic segment and at least one attached elastic segment for providing controlled stretch of the support strap during placement on the foot and during subsequent movement of the foot while the support is in place.

8. A plantar fascitis foot support apparatus, comprising:
   (a) a support strap for being positioned in a generally U-shaped configuration along the medial and lateral aspects of the ankle and extending under and supporting the plantar fascia region of the foot;
   (b) an ankle-encircling retention strap attached by its opposite ends to the support strap at a substantially right angle thereto for retaining the support strap in a supporting position against the plantar fascia region;
   (c) complementary and releasably-adjustable fastener elements carried by said retention strap and said support strap for permitting lengthwise adjustment of the support strap relative to the plantar fascia region of the foot, said fastener elements including:
      (i) a first fastener element carried by an outer surface of the retention strap;
      (ii) a second fastener element carried by an inner surface of the support strap for being adjustably-mated with the first fastener element for retaining the support strap and the retention strap in a desired position relative to each other;
      (iii) a third fastener element carried on an outer surface of the support strap; and
      (iv) a fastener cover carried by said retention strap and having a fourth fastener element carried on an inner surface thereof for mating with the third fastener element of the support strap.

9. A plantar fascitis foot support apparatus, comprising:
  (a) a support strap for being positioned in a generally U-shaped configuration along the medial and lateral aspects of the ankle and extending under and supporting the plantar fascia region of the foot,
  (b) an ankle-encircling retention strap attached by its opposite ends to the support strap at a substantially right angle thereto for retaining the support strap in a supporting position against the plantar fascia region;
  (c) first complementary and releasably-adjustable fastener elements carried by an outer surface of said retention strap and an inner surface of said support strap for permitting lengthwise adjustment of the support strap relative to the plantar fascia region of the foot; and
  (d) second complementary and releasably-adjustable fastener elements carried by an outer surface of said support strap and an inner surface of a cover carried by said retention strap for providing enhanced attachment force between the retention strap and the support strap.

10. A plantar fascitis support apparatus according to claim 9, wherein said cover is attached to said retention strap at one end of said cover.

11. A plantar fascitis support according to claim 9, wherein said first and second fastener elements comprise complementary hook and loop elements.

12. A method of treating plantar fascitis, and comprising the steps of:
  (a) positioning a support strap in a generally U-shaped configuration along the medial and lateral aspects of the ankle and extending under and supporting the plantar fascia region of the foot;
  (b) attaching an ankle-encircling retention strap by its opposite ends to the support strap at a substantially right angle thereto for retaining the support strap in a supporting position against the plantar fascia region;
  (c) providing in said support strap an inelastic segment and an attached elastic segment for providing controlled stretch of the support strap during placement on the foot and during subsequent movement of the foot while the support is in place;
  (d) adjusting the length of the support strap relative to the plantar fascia region of the foot for retaining the support strap and the retention strap in a desired position relative to each other.

* * * * *